United States Patent [19]
Krech, Jr.

[11] Patent Number: 5,807,317
[45] Date of Patent: Sep. 15, 1998

[54] TROCAR WITH CONCAVE CUTTING SURFACE

[75] Inventor: David L. Krech, Jr., Columbus, Miss.

[73] Assignee: Microtek Medical, Inc., Columbus, Miss.

[21] Appl. No.: 807,383

[22] Filed: Feb. 27, 1997

[51] Int. Cl.⁶ .................................................. A61M 27/00
[52] U.S. Cl. ........................... 604/51; 604/272; 606/185; 606/223
[58] Field of Search .................................... 606/167, 170, 606/159, 185, 223; 604/51, 272

[56] References Cited

U.S. PATENT DOCUMENTS

| | | |
|---|---|---|
| 1,599,059 | 9/1926 | Morton . |
| 2,899,960 | 8/1959 | Ginsburg ................................ 604/272 |
| 3,540,112 | 11/1970 | Knox ........................................ 29/414 |
| 4,384,942 | 5/1983 | Glowacki ........................... 204/129.46 |
| 4,398,910 | 8/1983 | Blake et al. ............................... 604/93 |
| 4,561,445 | 12/1985 | Berke et al. ............................ 128/642 |
| 4,777,096 | 10/1988 | Borysko ................................. 428/571 |
| 4,785,868 | 11/1988 | Koenig, Jr. .................................. 163/5 |
| 4,869,259 | 9/1989 | Elkins ..................................... 128/660 |
| 4,976,684 | 12/1990 | Broadnaz, Jr. ........................... 604/51 |
| 5,057,401 | 10/1991 | Borysko et al. ........................ 430/320 |
| 5,155,943 | 10/1992 | Matsutani et al. .................... 51/281 R |
| 5,178,628 | 1/1993 | Otsuka et al. .......................... 606/223 |
| 5,263,974 | 11/1993 | Matsutani et al. ...................... 606/223 |

FOREIGN PATENT DOCUMENTS

| | | |
|---|---|---|
| 0077312 | 10/1982 | European Pat. Off. . |
| 222799A | 5/1985 | Germany . |
| 45-31383 | 10/1970 | Japan . |
| 57-14437 | 1/1982 | Japan . |
| 149032A | 6/1988 | Japan . |
| 692718 | 11/1979 | Russian Federation . |
| 1680423 | 9/1991 | Russian Federation . |

*Primary Examiner*—Michael Powell Buiz
*Assistant Examiner*—Nancy Connolly Mulcare
*Attorney, Agent, or Firm*—Baker & Botts, L.L.P.

[57] ABSTRACT

An improved trocar is provided. The trocar includes a shaft having a first end and a second end with a bend therebetween. An attachment fixture is integral with the shaft at the first end. A concave cutting edge is formed at the second end.

7 Claims, 1 Drawing Sheet

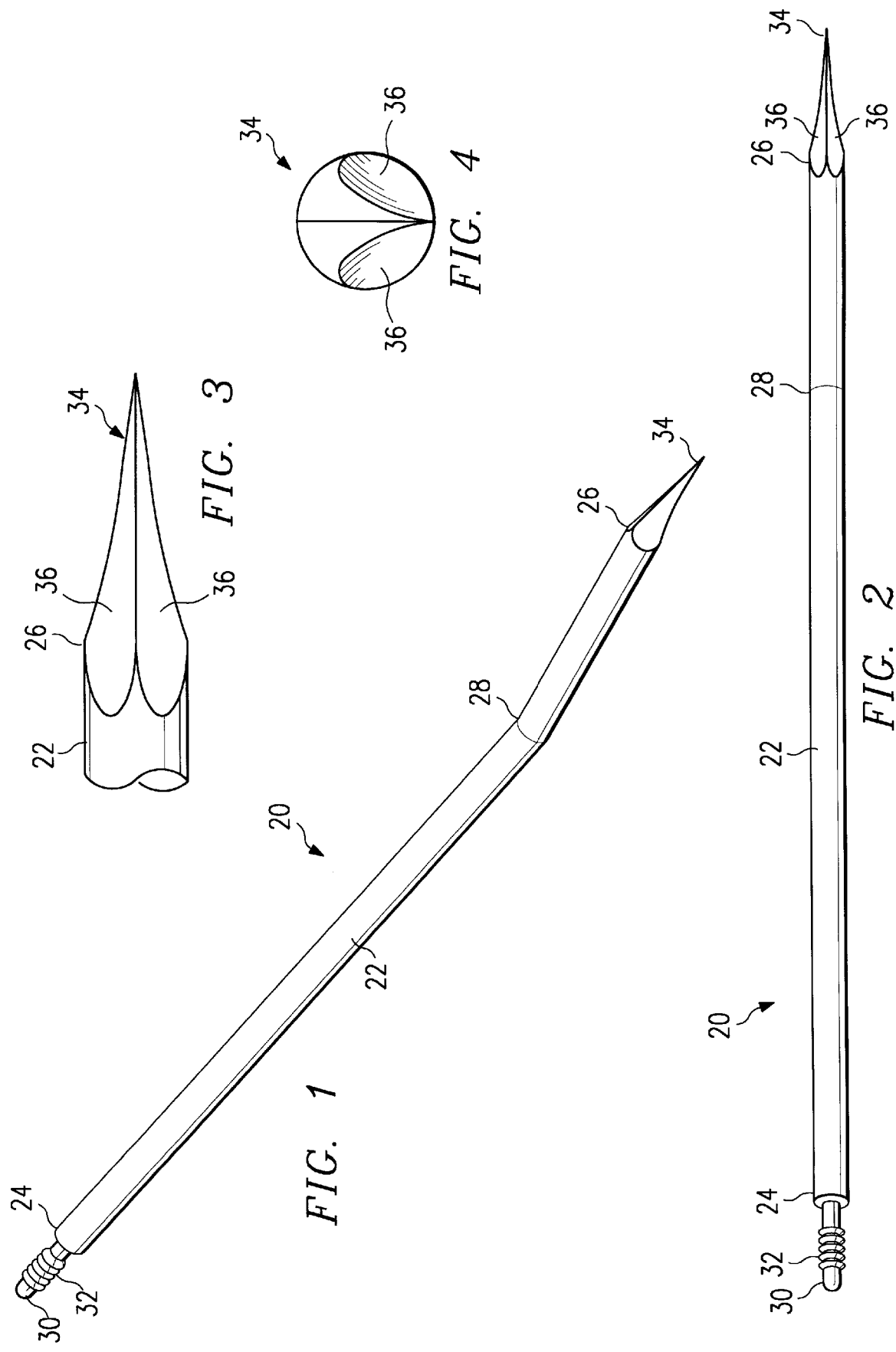

TROCAR WITH CONCAVE CUTTING SURFACE

TECHNICAL FIELD OF THE INVENTION

This invention relates generally to surgical instruments, and more particularly to a trocar with a concave cutting surface.

BACKGROUND OF THE INVENTION

In many surgical procedures, it is desirable to insert a drainage catheter into a patient's body proximate a surgical site in order to drain fluid away from such site. To accomplish this, the drainage catheter may be attached to needle-like device known as a trocar. The trocar is used to puncture the patient's body at an entry site, direct the drainage catheter through the body, and puncture the patient's body at an exit site. Afterwards, the trocar can be separated from the drainage catheter, which is then used to drain fluid. In light of the above, it can be seen that a cutting edge of a trocar is very important to its operation.

The cutting edges of previously developed trocars were formed by a grinding process which produced flat cutting surfaces. Such prior trocars were problematic for numerous reasons. For example, when these trocars were used, the flat cutting surfaces created jagged openings in a patient's body at the entry and exit sites. The jagged openings were difficult to sew up and also required a relatively long time to heal. Furthermore, it was very difficult to maintain a sharp edge on the flat cutting surfaces of prior trocars. Accordingly, excessive force was often needed to move such trocars through the tissue of a patient's body. This created a risk that the trocars would be misdirected in the tissue, thereby endangering sensitive organs in some cases.

SUMMARY OF THE INVENTION

In accordance with the present invention, the disadvantages and problems associated with previously developed trocars have been substantially reduced or eliminated.

According to an embodiment of the present invention, a trocar includes a shaft having a first end and a second end with a bend therebetween. An attachment fixture is integral with the shaft at the first end. A concave cutting edge is formed at the second end.

According to another embodiment of the present invention, a method of forming a trocar is provided. The method includes the following steps: providing a shaft having a first end and a second end with a bend therebetween, the shaft having an attachment fixture integral with the first end; and forming a concave cutting edge into the shaft at the second end.

The present invention provides various technical advantages over previously developed trocars. One technical advantage includes forming a cutting edge of a trocar by a milling process in order to create a concave cutting surface. The concave cutting surface provides a sharper edge which produces relatively "clean" openings at the entry and exit sites of a patient's body. In addition, a sharp edge is more easily maintained on the concave cutting surface. Accordingly, excessive force is not required to direct the trocar of the present invention through a patient's body, thereby reducing the risk that any vital organ of the patient will be punctured. Other technical advantages are readily apparent to one skilled in the art from the following figures, descriptions, and claims.

BRIEF DESCRIPTION OF THE DRAWINGS

For a more complete understanding of the present invention and for advantages thereof, reference is now made to the following description taken in conjunction with the accompanying drawings, wherein like reference numerals represent like parts, in which:

FIG. 1 illustrates a perspective view of a trocar formed according to an embodiment of the present invention;

FIG. 2 illustrates a plan view of the trocar shown in FIG. 1;

FIG. 3 illustrates an enlarged plan view of a cutting edge of the trocar shown in FIG. 1; and FIG. 4 illustrates an enlarged frontal view of the cutting edge of the trocar shown in FIG. 1.

DETAILED DESCRIPTION OF THE INVENTION

The present invention and its advantages are best understood by referring to FIGS. 1–4 of the drawings, like numerals being used for like and corresponding parts of the various drawings.

FIGS. 1 and 2 are perspective and plan views, respectively, of a trocar 20 formed according to an exemplary embodiment of the present invention. Trocar 20 may be formed of any suitable material, such as surgical quality stainless steel, which is sufficiently hard to hold a cutting edge and also sufficiently rigid to withstand twisting as trocar 20 is inserted and directed through a medium, such as animal (e.g., human) tissue.

Trocar 20 comprises a shaft 22 having a first end 24 and a second end 26. Shaft 22 may be substantially cylindrical, and formed in any suitable diameter, such as 3/32nds, 1/8th, 3/16ths, or 1/4th of an inch. The length of shaft 22 may vary according to its diameter. A bend 28 is preferably formed between first end 24 and second end 26 of shaft 22. The angle of bend 28 can be any suitable angle which allows or facilitates the movement, direction, or guidance of trocar 20 through a medium, such as animal (e.g., human) tissue.

An attachment fixture 30 can be formed integral to shaft 22 at first end 24. Attachment fixture 30 functions to attach a drainage catheter to trocar 20.

For this purpose, one or more threads 32 may be provided on attachment fixture 30. Attachment fixture 30 may have a substantially cylindrical shape of a suitable diameter to accommodate the size of the drainage catheter with which trocar 20 is used.

As shown in FIGS. 3 and 4, a cutting edge 34 is formed at the second end 26 of trocar 20. Cutting edge 34 can be produced by a milling process, which can be performed, for example, by a screw-type lathe. According to the present invention, the milling process results in concave cutting surfaces 36. Compared to the flat cutting surfaces of prior trocars, concave cutting surfaces 36 are sharper and better able to hold an edge.

In operation, a drainage catheter or tube may be attached to trocar 20 at attachment fixture 30. Trocar 30 may then be inserted into a patient's body proximate a surgical site. Because of the concave cutting surfaces 36, the opening created by trocar 20 at the point of insertion will be relatively smooth. Trocar 20 is then threaded through the tissue of a patient's body. The drainage catheter follows in the path of trocar 20. Trocar 20 exits a patient's body at another point proximate the surgical site. Like the point of entry, the point of exit will also be a relatively smooth opening. Trocar 20 is then completely removed from a patient's body and then detached from the drainage catheter. The drainage catheter can then be used to drain fluid from a patient's body proximate the surgical site.

Trocar 20 of the present invention provides numerous advantages over prior trocars. As described above, the openings created by trocar 20 at the point of entry and exit in a patient's body are relatively smooth, as opposed to the jagged openings created by prior trocars. These smooth openings are more easily sewn up, and will typically heal faster than jagged openings. Furthermore, insertion and movement of trocar 20 through a patient's body is facilitated due to the sharper concave cutting edges 36. Consequently, excessive force is not required to insert and direct trocar 20.

Although the present invention and its advantages have been described in detail, it should be understood that various changes, substitutions, and alterations can be made therein without departing from the spirit and scope of the invention as defined by the appended claims.

What is claimed is:

1. A trocar comprising a shaft having a first end and a second end with a bend therebetween, an attachment fixture integral with the shaft at the first end, and a concave cutting edge formed at the second end.

2. The trocar of claim 1, wherein the concave cutting edge comprises a first and a second concave cutting surface.

3. The trocar of claim 1, wherein the concave cutting edge is formed by a milling process.

4. The trocar of claim 1, wherein the trocar is formed of surgical quality stainless steel.

5. A trocar comprising a shaft having a first end and a second end with a bend therebetween, an attachment fixture integral with the shaft at the first end, and a cutting edge with a first and second concave cutting surfaces formed by a milling process.

6. A method of forming a trocar, comprising the steps of:

providing a shaft having a first end and a second end with a bend therebetween, the shaft having an attachment fixture integral with the first end; and forming a concave cutting edge into the shaft at the second end.

7. The method of claim 6, wherein the step of forming a concave cutting edge comprises the step of milling a first concave surface and a second concave surface into the second end of the shaft.

\* \* \* \* \*